United States Patent
Cannon et al.

(10) Patent No.: US 10,125,338 B2
(45) Date of Patent: Nov. 13, 2018

(54) FLAVOR AND FRAGRANCE COMPOSITIONS CONTAINING THIOPYRAN-CARBALDEHYDE

(71) Applicant: International Flavors & Fragrances Inc., New York, NY (US)

(72) Inventors: Robert Cannon, Fair Haven, NJ (US); Adam Jan Janczuk, Old Bridge, NJ (US); David O. Agyemang, Jackson, NJ (US); Zhen Chen, Aberdeen, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 2 days.

(21) Appl. No.: 15/338,758

(22) Filed: Oct. 31, 2016

(65) Prior Publication Data

US 2017/0051232 A1 Feb. 23, 2017

Related U.S. Application Data

(62) Division of application No. 14/546,462, filed on Nov. 18, 2014, now Pat. No. 9,510,612.

(51) Int. Cl.
| | | |
|---|---|---|
| *A61Q 11/00* | (2006.01) |
| *C11B 9/00* | (2006.01) |
| *A23G 4/06* | (2006.01) |
| *A23L 2/56* | (2006.01) |
| *A23L 27/20* | (2016.01) |
| *A61K 47/22* | (2006.01) |
| *A61K 8/49* | (2006.01) |
| *C07D 335/02* | (2006.01) |
| *A23L 27/29* | (2016.01) |

(52) U.S. Cl.
CPC ............... *C11B 9/008* (2013.01); *A23G 4/06* (2013.01); *A23L 2/56* (2013.01); *A23L 27/2052* (2016.08); *A23L 27/29* (2016.08); *A61K 8/4986* (2013.01); *A61K 47/22* (2013.01); *A61Q 11/00* (2013.01); *C07D 335/02* (2013.01); *A23V 2002/00* (2013.01); *A61K 2800/40* (2013.01)

(58) Field of Classification Search
CPC ......... A23L 2/56; A23L 27/29; C07D 335/02; A61K 8/4986; A61K 47/22; C11B 9/008; A61Q 11/00
See application file for complete search history.

(56) References Cited

PUBLICATIONS

Kleipool et al., Z. Lebensm. Unters.-Forsch. 161, 231-238 (1976).*
Badings et al., Z. Lebensm. Unters.-Forsch, 161, 53-59 (1976).*
J. Schaefer, Development of Instrumental Methods for Measuring Odour Levels in Intensive Livestock Buidings, 513-535 (no date provided).*

* cited by examiner

*Primary Examiner* — Lezah Roberts
(74) *Attorney, Agent, or Firm* — Xufan Tseng; Martin Zhang; Elizabeth M. Stover

(57) ABSTRACT

The present invention relates to the novel flavor and fragrance use of 2,6-dipropyl-5,6-dihydro-2H-thiopyran-3-carbaldehyde.

5 Claims, No Drawings

FLAVOR AND FRAGRANCE COMPOSITIONS CONTAINING THIOPYRAN-CARBALDEHYDE

STATUS OF RELATED APPLICATIONS

This application is a divisional of U.S. Ser. No. 14/546,462, filed Nov. 18, 2014, now allowed, the contents hereby incorporated by reference as if set forth in its entirety.

FIELD OF THE INVENTION

The present invention relates to the incorporation and use of a new chemical entity as a flavor and fragrance material.

BACKGROUND OF THE INVENTION

There is an ongoing need in the flavor industry for flavor chemicals that enhance or provide new flavors for food preparations. There is a similar ongoing need for fragrance chemicals to give perfumers and other persons the ability to create new fragrances for perfumes, colognes and personal care products. Those with skill in the art appreciate how differences in the chemical structures of the molecules can result in significant differences in the odor, notes and characteristics. The identification of structural variations and discovery of new chemicals enable the creation of new flavors and fragrances.

It has long been known that sulphur compounds may possess repulsive odor, resulting in off-flavor in food and contributing to air pollution (See, Badings, H. T. et al. *Z. Lebensm. Unters.-Forsch.* 1976, 161, pages 53-59; Schaefer, J. *Comm. Eur. Communities* 1980, pages 513-535). Sulphur compounds, for example, were observed in hen manure. One such compound 2,6-dimethyl-5,6-dihydro-2H-thiopyran-3-carbaldehyde was also detected in the air of laying hen houses and was identified to play important roles in the odors of both hen manure and laying hen houses (See, Schaefer, J.). In a study of the formation of sulphur compounds during the preparation or storage of food products, a model system testing the reaction of hydrogen sulphide and 2-butenal was proposed and investigated. A number of sulphur compounds were identified and their off-odor properties were reported. 2,6-Dimethyl-5,6-dihydro-2H-thiopyran-3-carbaldehyde was again found and described as having onion and metallic odors. In the model, more sulphur compounds including 2,6-dipropyl-5,6-dihydro-2H-thiopyran-3-carbaldehyde were proposed. However, none of the proposed molecules was isolated and/or confirmed and no odor assessment was made (See, Badings, H. T. et al.; Kleipool, R. J. C. et al. *Z. Lebensm. Unters.-Forsch.* 1976, 161, pages 231-238).

It has now been found, unexpectedly and contrary to what might be expected, that 2,6-dipropyl-5,6-dihydro-2H-thiopyran-3-carbaldehyde possesses surprisingly strong fruity and tropical organoleptic notes and is therefore particularly useful in enhancing the flavor of foodstuff, chewing gums, dental and oral hygiene products and medicinal products. It is also found to be useful in enhancing, improving or modifying the fragrance of perfumes, colognes, toilet waters, personal products, fabric care products, and the like.

SUMMARY OF THE INVENTION

The present invention is directed to a method of improving, enhancing or modifying a flavor or a fragrance composition through the addition of an olfactory acceptable amount of 2,6-dipropyl-5,6-dihydro-2H-thiopyran-3-carbaldehyde represented by Formula I set forth below:

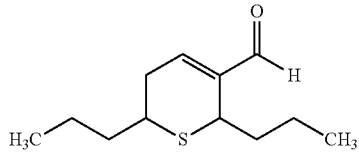

Formula I

Another embodiment of the invention is directed to a flavor or a fragrance composition comprising 2,6-dipropyl-5,6-dihydro-2H-thiopyran-3-carbaldehyde.

Another embodiment of the invention is directed to a composition comprising 2,6-dipropyl-5,6-dihydro-2H-thiopyran-3-carbaldehyde and a material selected from the group consisting of a foodstuff, a chewing gum, a dental product, an oral hygiene product, a medicinal product, a perfume, a cologne, toilet water, a cosmetic product, a personal care product, a fabric care product, a cleaning product and an air freshener.

These and other embodiments of the present invention will be apparent by reading the following specification.

DETAILED DESCRIPTION OF THE INVENTION 2,6-Dipropyl-5,6-dihydro-2H-thiopyran-3-carbaldehyde of the present invention may be prepared with 3-(acetylthio)-hexanal. Its preparation is detailed below in Example I. Materials were purchased from Aldrich Chemical Company unless noted otherwise.

Those with skill in the art will recognize that the compound of the present invention contains a chiral center, thereby providing a number of isomers of the claimed compound. It is intended herein that the compound of the present invention includes isomeric mixtures as well as individual isomers that may be separated using techniques known to those having skill in the art. Suitable techniques include chromatography such as high performance liquid chromatography, referred to as HPLC, particularly silica gel chromatograph, and gas chromatography trapping known as GC trapping. Yet, commercial versions of such products are mostly offered as mixtures.

2,6-Dipropyl-5,6-dihydro-2H-thiopyran-3-carbaldehyde is found to have unexpected strong and long-lasting fruity and tropical notes, which are shown to be advantageous for its use in augmenting or imparting taste enhancement or somatosensory effect to foodstuffs, chewing gums, dental and oral hygiene products and medicinal products by providing flavor enhancement and a preferred overall flavor profile. The present invention further relates to a process of augmenting or imparting taste or somatosensory effect to foodstuffs, chewing gums, dental and oral hygiene products and medicinal products by adding 2,6-dipropyl-5,6-dihydro-2H-thiopyran-3-carbaldehyde.

When 2,6-dipropyl-5,6-dihydro-2H-thiopyran-3-carbaldehyde is used in a flavoring composition, it can be combined with conventional flavoring materials or adjuvants, which are well known in the art and have been extensively described in the past. Conventional flavoring materials include saturated fatty acids, unsaturated fatty acids, amino acids; alcohols including primary and secondary alcohols; esters; carbonyl compounds including ketones; aldehydes; lactones; cyclic organic materials including benzene derivatives, acyclic compounds, heterocyclies such as furans, pyridines, pyrazines and the like; other sulfur-containing compounds including thiols, sulfides, disulfides and the like; proteins; lipids; carbohydrates; so-called flavor potentiators such as monosodium glutamate; magnesium glutamate, calcium glutamate, guanylates and inosinates; natural flavoring materials such as hydrolyzates, cocoa, vanilla and caramel; essential oils and extracts such as anise oil, clove oil and the like; and artificial flavoring materials such as vanillin, ethyl vanillin and the like. Requirements for adjuvants include: (1) that they be non-reactive with 2,6-dipropyl-5,6-dihydro-2H-thiopyran-3-carbaldehyde; (2) that they be organoleptically compatible with 2,6-dipropyl-5,6-dihydro-2H-thiopyran-3-carbaldehyde, whereby the flavor of the ultimate consumable product to which 2,6-dipropyl-5,6-dihydro-2H-thiopyran-3-carbaldehyde is added is not detrimentally affected by the use of the adjuvants; and (3) that they be ingestible acceptable and thus nontoxic or otherwise non-deleterious. In addition, other flavor materials, vehicles, stabilizers, thickeners, surface active agents, conditioners and flavor intensifiers can also be included.

The use of 2,6-dipropyl-5,6-dihydro-2H-thiopyran-3-carbaldehyde is further applicable in current perfumery products, including the preparation of perfumes and colognes, the perfuming of personal care products such as soaps, shower gels, and hair care products, fabric care products, air fresheners, and cosmetic preparations. The present invention can also be used to perfume cleaning agents, such as, but not limited to detergents, dishwashing materials, scrubbing compositions, window cleaners and the like.

In these preparations, 2,6-dipropyl-5,6-dihydro-2H-thiopyran-3-carbaldehyde can be used alone or in combination with other perfuming compositions, solvents, adjuvants and the like. The nature and variety of the other ingredients that can also be employed are known to those with skill in the art. Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

2,6-Dipropyl-5,6-dihydro-2H-thiopyran-3-carbaldehyde can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), (3,3-dimethylcyclohexyl)ethyl ethyl propane-1,3-dioate (Applelide), (E/Z)-1-ethoxy-1-decene (Arctical), 2-ethyl-4-(2,2,3-trimethyl-3-cyclopenten-1-yl)-2-buten-1-ol (Bacdanol), 2-methyl-3-[(1,7,7-trimethylbicyclo[2.2.1]hept-2-yl)-oxy] exo-1-propanol (Bornafix), 1,2,3,5,6,7-hexahydro-1,1,2,3,3-pentamethyl-4H-inden-4-one (Cashmeran), trimethylcyclopentenylmethyloxabicyclooctane (Cassiffix), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (Helional), 1-(2,6,6-trimethyl-2-cyclohexen-1-yl)-1,6-heptadien-3-one (Hexalon), (Z)-3-hexenyl-2-hydroxybenzoate (Hexenyl Salicylate, CIS-3), 4-(2,6,6-trimethyl-2-cyclohexen-1-yl)-3-buten-2-one (Ionone α), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methyl-pentyl) cyclohexene-1-carboxaldehyde (Lyral), 3-methyl-4-(2,6,6-trimethyl-2-cyclohexen-1-yl)-3-buten-2-one (Methyl Ionone γ), 1-(2,6,6-trimethyl-2-cyclohexen-1-yl) pent-1-en-3-one (Methyl Ionone α Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo[7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl) cyclohex-3-ene-1-carboxaldehyde (Precyclemone B), 4-methyl-8-methylene-2-adamantanol (Prismantol), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), 4-tert-butylcyclohexyL acetate (Vertenex), acetyl cedrene (Vertofix), 3,6/4,6-dimethylcyclohex-3-ene-1-carboxaldehyde (Vertoliff), and (3Z)-1-[(2-methyl-2-propenyl)oxy]-3-hexene (Vivaldie).

The term "foodstuff" as used herein includes both solid and liquid ingestible materials for man or animals, which materials usually do, but need not, have nutritional value. Thus, foodstuffs include meats, gravies, soups, convenience foods, malt, alcoholic and other beverages, milk and dairy products, seafood, including fish, crustaceans, mollusks and the like, candies, vegetables, cereals, soft drinks, snacks, dog and cat foods, other veterinary products and the like.

The terms "flavor composition" and "flavor formulation" mean the same and refer to a consumer composition that produces a pleasant or desired flavor. The flavor composition contains a compound or a mixture of compounds. The flavor composition of the present invention is a consumer composition comprising 2,6-dipropyl-5,6-dihydro-2H-thiopyran-3-carbaldehyde.

The terms "fragrance composition", "fragrance formulation" and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance composition of the present invention is a consumer composition comprising 2,6-dipropyl-5,6-dihydro-2H-thiopyran-3-carbaldehyde. The fragrance composition of the present invention comprises 2,6-dipropyl-5,6-dihydro-2H-thiopyran-3-carbaldehyde and further a complementary fragrance compound as defined above.

The terms "fragrance product" and "perfumery product" mean the same and refer to a consumer product containing a fragrance ingredient that adds fragrance or masks malodor. Fragrance products may include, for example, perfumes, colognes, bar soaps, liquid soaps, shower gels, foam baths, cosmetics, skin care products such as creams, lotions and shaving products, hair care products for shampooing, rinsing, conditioning, bleaching, coloring, dyeing and styling, deodorants and antiperspirants, feminine care products such as tampons and feminine napkins, baby care products such as diapers, bibs and wipes, family care products such as bath tissues, facial tissues, paper handkerchiefs or paper towels, fabric products such as fabric softeners and fresheners, air care products such as air fresheners and fragrance delivery systems, cosmetic preparations, cleaning agents and disinfectants such as detergents, dishwashing materials, scrubbing compositions, glass and metal cleaners such as window cleaners, countertop cleaners, floor and carpet cleaners, toilet cleaners and bleach additives, washing agents such as all-purpose, heavy duty, and hand washing or fine fabric washing agents including laundry detergents and rinse additives, dental and oral hygiene products such as toothpastes, tooth gels, dental flosses, denture cleansers, denture adhesives, dentifrices, tooth whitening and mouthwashes, health care and nutritional products and food products such as snack and beverage products. The fragrance product of the present invention is a consumer product that contains 2,6-dipropyl-5,6-dihydro-2H-thiopyran-3-carbaldehyde. The fragrance product of the present invention contains 2,6-dipropyl-5,6-dihydro-2H-thiopyran-3-carbaldehyde and further a complementary fragrance compound as defined above.

The term "improving" is understood to mean raising a flavor or fragrance composition to a more desirable character. The term "enhancing" is understood to mean making the flavor or fragrance composition greater in effectiveness or providing the flavor or fragrance composition with an improved character. The term "modifying" is understood to mean providing the flavor or fragrance composition with a change in character.

The term "olfactory acceptable amount" is understood to mean the amount of a compound in a flavor or fragrance formulation, wherein the compound will contribute its individual olfactory characteristics. However, the olfactory effect of the flavor or fragrance formulation will be the sum of effect of each of the flavor or fragrance ingredients. Thus, 2,6-dipropyl-5,6-dihydro-2H-thiopyran-3-carbaldehyde can be used to improve or enhance the aroma characteristics of the flavor or fragrance formulation, or by modifying the olfactory reaction contributed by other ingredients in the formulation. The olfactory acceptable amount may vary depending on many factors including other ingredients, their relative amounts and the olfactory effect that is desired.

Generally, the olfactory acceptable amount of 2,6-dipropyl-5,6-dihydro-2H-thiopyran-3-carbaldehyde employed in a flavor composition is greater than about 0.1 parts per billion by weight, preferably from about 1 part per billion to about 1000 parts per million by weight, more preferably from about 10 parts per billion to about 100 parts per million by weight, even more preferably from about 100 parts per billion to about 10 parts per million by weight. The olfactory acceptable amount of 2,6-dipropyl-5,6-dihydro-2H-thiopyran-3-carbaldehyde employed in a fragrance composition varies from about 0.005 to about 70 weight percent, preferably from 0.05 to about 50 weight percent, more preferably from about 0.5 to about 25 weight percent, and even more preferably from about 1 to about 10 weight percent. Those with skill in the art will be able to employ the desired amount to provide desired flavor or fragrance effect and intensity. In addition to the compound of the present invention, other materials can also be used in conjunction with the flavor or fragrance composition to encapsulate and/or deliver the flavor or fragrance. Some well-known materials are, for example, but not limited to, polymers, oligomers, other non-polymers such as surfactants, emulsifiers, lipids including fats, waxes and phospholipids, organic oils, mineral oils, petrolatum, natural oils, perfume fixatives, fibers, starches, sugars and solid surface materials such as zeolite and silica.

When used in a fragrance formulation these ingredients provide additional notes to make a fragrance formulation more desirable and noticeable, and add the perception of value. The odor qualities found in these materials assist in beautifying and enhancing the finished accord as well as improving the performance of the other materials in the fragrance.

In addition, the compounds of the present invention are also surprisingly found to provide superior ingredient performance and possess unexpected advantages in malodor counteracting applications such as body perspiration, environmental odor such as mold and mildew, bathroom, and etc. The compounds of the present invention substantially eliminate the perception of malodors and/or prevent the formation of such malodors, thus, can be utilized with a vast number of functional products.

Examples of the functional products are provided herein to illustrate the various aspects of the present invention. However, they do not intend to limit the scope of the present invention. The functional products may include, for example, a conventional room freshener (or deodorant) composition such as room freshener sprays, an aerosol or other spray, fragrance diffusers, a wick or other liquid system, or a solid, for instance candles or a wax base as in pomanders and plastics, powders as in sachets or dry sprays or gels, as in solid gel sticks, clothes deodorants as applied by washing machine applications such as in detergents, powders, liquids, whiteners or fabric softeners, fabric refreshers, linen sprays, closet blocks, closet aerosol sprays, or clothes storage areas or in dry cleaning to overcome residual solvent notes on clothes, bathroom accessories such as paper towels, bathroom tissues, sanitary napkins, towellets, disposable wash cloths, disposable diapers, and diaper pail deodorants, cleansers such as disinfectants and toilet bowl cleaners, cosmetic products such as antiperspirant and deodorants, general body deodorants in the form of powders, aerosols, liquids or solid, or hair care products such as hair sprays, conditioners, rinses, hair colors and dyes, permanent waves, depilatories, hair straighteners, hair groom applications such as pomade, creams and lotions, medicated hair care products containing such ingredients as selenium sulphide, coal tar or salicylates, or shampoos, or foot care products such as foot powders, liquids or colognes, after shaves and body lotions, or soaps and synthetic detergents such as bars, liquids, foams or powders, odor control such as during manufacturing processes, such as in the textile finishing industry and the printing industry (inks and paper), effluent control such as in processes involved in pulping, stock yard and meat processings, sewage treatment, garbage bags, or garbage disposal, or in product odor control as in textile finished goods, rubber finished goods or car fresheners, agricultural and pet care products such as dog and hen house effluents and domestic animal and pet care products such as deodorants, shampoo or cleaning agents, or animal litter material and in large scale closed air systems such as auditoria, and subways and transport systems.

Thus, it will be seen that the composition of the invention is usually one in which the malodor counteractant is present together with a carrier by means of which or from which the malodor counteractant can be introduced into air space wherein the malodor is present, or a substrate on which the malodor has deposited. For example, the carrier can be an aerosol propellant such as a chlorofluoro-methane, or a solid such as a wax, plastics material, rubber, inert powder or gel. In a wick-type air freshener, the carrier is a substantially odorless liquid of low volatility. In several applications, a composition of the invention contains a surface active agent or a disinfectant, while in others, the malodor counteractant is present on a fibrous substrate. In many compositions of the invention there is also present a fragrance component which imparts a fragrance to the composition. The fragrances stated above can all be employed.

Malodor counteracting effective amount is understood to mean the amount of the inventive malodor counteractant employed in a functional product that is organoleptically effective to abate a given malodor while reducing the combined intensity of the odor level, wherein the given malodor is present in air space or has deposited on a substrate. The exact amount of malodor counteractant agent employed may vary depending upon the type of malodor counteractant, the type of the carrier employed, and the level of malodor counteractancy desired. In general, the amount of malodor counteractant agent present is the ordinary dosage required to obtain the desired result. Such dosage is known to the skilled practitioner in the art. In a preferred embodiment, when used in conjunction with malodorous solid or liquid functional products, e.g., soap and detergent, the compounds of the present invention may be present in an amount ranging from about 0.005 to about 50 weight percent, preferably from about 0.01 to about 20 weight percent, and more preferably from about 0.05 to about 5 weight percent, and when used in conjunction with malodorous gaseous functional products, the compounds of the present invention may be present in an amount ranging from about 0.1 to 10 mg per cubic meter of air.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, mL is understood to be milliliter, g is understood to be gram, mol is understood to be mole and mmol is understood to be millimole. IFF as used in the examples is understood to mean International Flavors & Fragrances Inc., New York, N.Y., USA.

Example I

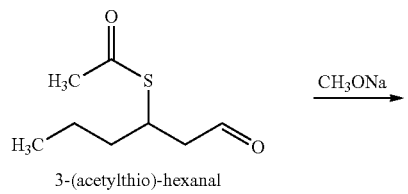

3-(acetylthio)-hexanal

CH₃ONa →

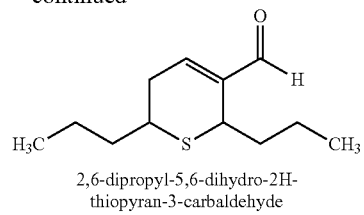

2,6-dipropyl-5,6-dihydro-2H-thiopyran-3-carbaldehyde

Preparation of 2,6-Dipropyl-5,6-dihydro-2H-thiopyran-3-carbaldehyde (Formula I)

Sodium methoxide (CH₃ONa) (16.2 g, 0.3 mol) was dissolved in methanol (MeOH) (100 mL). 3-(Acetylthio)-hexanal (25 g, 0.1 mol) was added dropwise. After the addition was complete, the reaction mixture was stirred at room temperature for additional 2 hours. Ice water (200 mL) was then added and the reaction mixture was acidified with hydrogen chloride (HCl) (10%) to pH 2. The resulting mixture was extracted with ethyl acetate (EtOAc) (200 mL). The organic layer was washed successively with brine, sodium bicarbonate solution (NaHCO₃) (10%) and brine, dried and concentrated to provide a crude product. The crude product was distilled and further purified with a silica gel column (ethyl acetate/hexanes) to afford 2,6-dipropyl-5,6-dihydro-2H-thiopyran-3-carbaldehyde (12 g).

¹H NMR (CDCl₃, 400 MHz): 9.32 (s, 1H), 6.79 (dd, 1H, J=5.3, 2.8 Hz), 3.51 (m, 1H), 2.92-3.05 (m, 1H), 2.61-2.75 (m, 1H), 2.22-2.38 (m, 1H), 1.35-1.76 (m, 8H), 0.95 (t, 3H, J=7.1 Hz), 0.93 (t, 3H, J=6.9 Hz).

2,6-Dipropyl-5,6-dihydro-2H-thiopyran-3-carbaldehyde (1% in water) was described as having fruity, green, cassis, savory and spicy characters.

Example II

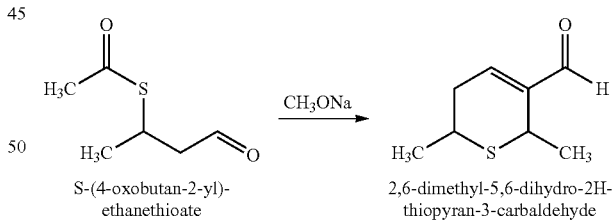

S-(4-oxobutan-2-yl)-ethanethioate

CH₃ONa →

2,6-dimethyl-5,6-dihydro-2H-thiopyran-3-carbaldehyde

Preparation of 2,6-Dimethyl-5,6-dihydro-2H-thiopyran-3-carbaldehyde (Formula II)

2,6-Dimethyl-5,6-dihydro-2H-thiopyran-3-carbaldehyde (4.8 g) was similarly prepared using S-(4-oxobutan-2-yl)-ethanethioate (100 g, 0.684 mol).

¹H NMR (CDCl₃, 500 MHz): 9.33 (s, 1H), 6.80 (dd, J=5.4, 2.5 Hz, 1H), 3.70 (q, J=6.9 Hz, 1H), 3.10-3.18 (m, 1H), 2.67-2.74 (m, 1H), 2.24-2.40 (m, 1H), 1.47 (d, J=6.9 Hz, 3H), 1.34 (d, J=6.6 Hz, 3H)

Example III

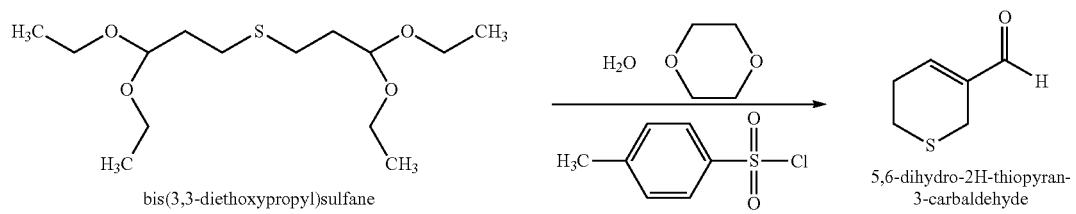

Preparation of 5,6-Dihydro-2H-thiopyran-3-carbaldehyde (Formula III)

Bis(3,3-diethoxypropyl)sulfane (50 g, 0.17 mol), water (69.4 mL, 3.855 mol), p-toluenesulfonyl chloride (1.619 g, 8.49 mmol) and 1,4-dioxane (100 mL, 1.174 mol) were combined and stirred at 80° C. for about 2 hours. The reaction was cooled to room temperature. Water was added and the reaction mixture was extracted with diethyl ether (($C_2H_5$)$_2$O). The organic layer was washed successively with saturated sodium bicarbonate solution, water and brine, and then dried and concentrated to provide a crude product. The crude product was further purified with a silica gel column (ethyl acetate/hexanes, 1:20) to afford 5,6-dihydro-2H-thiopyran-3-carbaldehyde (3.2 g).

$^1$H NMR (CDCl$_3$, 400 MHz): 9.37 (s, 1H), 6.86-6.96 (m, 1H), 3.29-3.36 (m, 2H), 2.79 (t, J-5.6 Hz, 2H), 2.63-2.72 (m, 2H)

Example IV

A series of concentrations in water for each of the above compounds (i.e., Formula I-III) were prepared. The organoleptic properties for each compound at each concentration were evaluated and are reported in the following:

| Concentration (ppm) | Formula I | Formula II | Formula III |
|---|---|---|---|
| 0.1 | Nutty, slightly fruity and tropical | Barely detectable | Weak and slightly metallic |
| 0.5 | Fresh, fruity and slightly jammy | Weak, chlorine-like, sulfury and slightly chemical | Garbage-like and rotten |
| 1 | Fruity, tropical and jammy | Slightly old onion-like, chemical and bitter | Potato-like and rotten |
| 10 | Sour cream and creamy | Sulfury, gasoline-like and onion-like. | Overcooked vegetable-like and egg yolk-like |

At all concentrations tested, Formula I exhibited highly desirable fruity, tropical and creamy notes, and Formula II and Formula III exhibited repulsive off-notes.

What is claimed is:

1. A method of improving, enhancing or modifying a flavor composition through the addition of an olfactory acceptable amount of 2,6-dipropyl-5,6-dihydro-2H-thiopyran-3-carbaldehyde, wherein the olfactory acceptable amount is greater than about 0.1 parts per billion by weight of the flavor composition.

2. The method of claim 1, wherein the flavor composition is added to a material selected from the group consisting of a foodstuff, a chewing gum, a dental product, an oral hygiene product and a medicinal product.

3. The method of claim 1, wherein the olfactory acceptable amount is from about 1 part per billion to about 1000 parts per million by weight of the flavor composition.

4. The method of claim 1, wherein the olfactory acceptable amount is from about 10 parts per billion to about 100 parts per million by weight of the flavor composition.

5. The method of claim 1, wherein the olfactory acceptable amount is from about 100 parts per billion to about 10 parts per million by weight of the flavor composition.

* * * * *